United States Patent [19]

Arena

[11] 4,274,980

[45] Jun. 23, 1981

[54] CHITIN- AND CHITOSAN-BASED IMMOBILIZED METAL CATALYSTS

[75] Inventor: Blaise J. Arena, Des Plaines, Ill.

[73] Assignee: UOP Inc., Des Plaines, Ill.

[21] Appl. No.: 83,926

[22] Filed: Oct. 11, 1979

[51] Int. Cl.$^3$ .............................................. B01J 31/02
[52] U.S. Cl. .................................... 252/430; 585/276; 585/277
[58] Field of Search ......................... 252/430; 585/277

[56] References Cited

U.S. PATENT DOCUMENTS

| 3,635,818 | 1/1972 | Muzzarelli | 210/656 |
| 4,111,838 | 9/1978 | Schaeffer | 252/430 |

OTHER PUBLICATIONS

Chem. Absts., vol. 76 (1972), p. 346, #13192b.
Talanta, vol. 16, pp. 1571–1577 (1969).

*Primary Examiner*—John F. Niebling
*Attorney, Agent, or Firm*—James R. Hoatson, Jr.; Raymond H. Nelson; William H. Page, II

[57] ABSTRACT

A composition comprising chitin or chitosan bearing a metal or mixture of metals deposited thereon in a highly dispersed state so as to immobilize said metal or mixture of metals is an effective catalyst for processes in which said metal or mixture of metals shows catalytic properties.

2 Claims, No Drawings

CHITIN- AND CHITOSAN-BASED IMMOBILIZED METAL CATALYSTS

BACKGROUND OF THE INVENTION

Metals are used as catalysts in a diversity of chemical processes. Ideally, it is desired to have such metals in as finally dispersed a state as possible so as to maximize catalytic activity. When metals are used in their most highly dispersed state, a batch-type process is often employed. Removal of the catalyst in subsequent processing is disadvantageous because of attending loss of metal and the necessity for costly separation stage. Therefore, metals commonly are deposited on an appropriate supporting medium in a more discrete fashion, for example, as extrusions, tablets, pellets, etc. Utilization of the metal in such a form permits continuous process, but it is found that the metal is not in such a finally dispersed state as otherwise possible. Furthermore, transport phenomena become important because much of the metal is in the interior of the supporting medium and not on its surface.

For such reasons it is highly desirable to have a metal, when used as a catalyst, in a highly dispersed state largely on the surface of the supporting medium, but with the medium of such a nature that it has the properties necessary for its use in a continuous process.

SUMMARY OF THE INVENTION

An object of this invention is to make available a preparation of metals in a highly dispersed state on organic supports possessing good mechanical and liquid flow properties. An embodiment of this invention is a composition comprising chitin or chitosan bearing a metal deposited thereon in a highly dispersed state so as to immobilize and retain said metal in a flowing liquid system. In a more specific embodiment the metal is palladium or platinum in a reduced oxidation state.

DESCRIPTION OF THE INVENTION

Chitin is a polysaccharide availabe in large quantities from the shells of crustaceans, a waste product of the fishing industry, and is the polymer of N-acetylglucosamine,

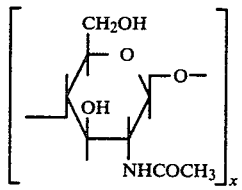

Deacetylation of chitin leads to chitosan. Both chitin and chitosan have good mechanical strength, and liquids show good flow properties in a bed or column of these polysaccharides. Furthermore, both chitin and chitosan complex or bind with metals. Chelation of a single metal ion by several—$NH_2$ or —$NHCOCH_3$ groups effectively isolates each metal ion from its neighbors. If such isolation is maintained, wholly or in large part, during sebsequent reduction of the metal to its zero-valent state, then such metals may be found in a highly dispersed state largely on the surface of the polysaccharide, thereby being relatively available to flowing liquids. Therefore, chitin and chitosan should be useful as metal supports in catalytic processes. Indeed, this invention demonstrates the veracity of such an hypothesis.

Catalytic processes for which metals commonly are employed include, for example hydrogenation, isomerization, and oxidation. When metal catalysts are supported on chitin or chitosan such catalytic systems may show substantially different and desirable characteristics in some catalytic processes, and therefore the catalyst systems of this invention may have advantages when compared with conventional catalyst systems, for example, metals supported on an inorganic oxide such as alumina.

The chitin or chitosan used in this invention may be in the form of a powder, flakes, or may even be granular in form. Both chitin and chitosan readily absorb metals from aqueous solutions. Since chitin normally is about 85% acetylated, it is to be expected that chitin has a lower capacity to absorb metal ions than does chitosan. Nonetheless, chitin does show appreciable absorptive capability toward some metals.

Although a diversity of metals can be absorbed by chitin or chitosan, Group VIII metals are of particular importance and interest because of their catalytic properties and usage. Within this group iron, cobalt, nickel, ruthenium, rhenium, palladium and platinum are of prime interest, although osmium and iridium also may be used, but not necessarily with equivalent results. These metals may be used in the valence state exhibited after absorption, which generally is from about 1 to about 4. Alternately, the absorbed metal may be reduced wholly or in part to its zero-valent state. Commonly, a major portion, by which is meant 51% or more, of the metal will be in the zero-valent state. The oxidation state of the metal dispersed on chitin or chitosan may depend on which polysaccharide is used and also may depend on the intended use of the catalyst system thereafter. For example, if the support metal system is to be used in hydrogenation, a zero-valent state generally is desired. On the other hand, if the supported metal system is to be used in a catalytic oxidation process, a higher oxidation state is desired.

It is to be understood that several metals in varying ratios may be deposited either concurrently or serially to give a mixed-metal impregnated chitin or chitosan. Similarly, the impregnated metal may be reduced only partly to give a polysaccharide bearing a mixture of oxidation states of the metal or metals deposited thereon.

Absorption of the metal is effected simply by contacting chitin or chitosan in a suitable physical form with an aqueous solution of the metal salt, preferably with mixing to ensure good contact. The conditions of contacting are not critical so long as the chitin or chitosan is not degraded, nor their absorptive capacity appreciably impaired, and the salt of, or acid containing, the metal remains in solution. To avoid degradation of chitin or chitosan, concentrated mineral acids (above about 1 molar) and caustic (above about 20%) at temperatures above about 100° C. should be avoided. After mixing, the metal impregnated polysaccharide is separated and washed to remove loosely adhereing excess metal.

The chitin or chitosan bearing the metal in the highly dispersed state may be used per se if the metal is to be used in other than its zero-valent state. If the metal is to be used subsequently in its zero-valent state, it is further treated with a reducing agent, for example, a reducing sugar, such as glucose, or formaldehyde. Frequently the reducing agent may be hydrogen. Where appropriate the reducing agent is removed by suitable means before the catalyst is employed for its intended use. For example, where glucose or formaldehyde is used the metal impregnated chitin or chitosan may be washed with water to remove the reducing agent. In contrast, where hydrogen is used and the catalyst is intended to be used in hydrogenation, no further treatment is necessary and reduction often can be done advantageously in situ. The concentration of metals on chitin or chitosan, whether the metals be in a zero-valent state or otherwise, may range from about 0.01 to about 10% by weight depending upon its intended use, the metal employed, and the salt used in the preparation of the supported catalyst system.

Although an object of this invention is to provide materials showing improved properties when used as a bed or column in continuous processes, it is apparent to a skilled artisan that the materials of this invention are eminently usable advantageously in conventional batch processes. For example, if the chitin or chitosan based metal catalyst system be in the form of a fine powder, these may be employed in stirred reactors but with the advantage that the catalyst shows improved filtration properties. Therefore, the catalyst can be recovered with little or no loss using relatively simple, inexpensive separation methods.

The catalyst of this invention may be advantageously used in continuous processes. Thus, when used as a bed or column the catalysts show good mechanical strength, retaining their integrity over long periods of time under diverse reaction conditions. The catalysts of this invention also exhibit good properties toward flowing liquids whether used in a downflow or upflow system.

The examples below merely serve to illustrate the invention described herein and are not necessarily intended to be construed as limitations thereof.

EXAMPLE 1

Palladium chloride, 0.4 g, dissolved in 20 ml of 2 M hydrochloric acid was stirred with 1.0 g of coarse chitosan flakes for ten minutes. The solid was then removed by filtration and washed with 100 ml of deionized water. The washed material was suspended in 10 ml of deionized water to which was added 20 ml of 2% potassium hydroxide and 20 ml formaldehyde. This suspension was stirred at 50° C. for 15 minutes, after which the palladium impregnated chitosan was filtered, washed with 100 ml of deionized water, and dried for 16 hours at 50° C. under vacuum. The product upon analysis contained 5.0% palladium.

EXAMPLE 2

A solution of 0.8 g palladium chloride in 20 ml of 2 M hydrochloric acid was stirred with 2.0 g of chitin powder for 30 minutes. The solid, removed by filtration, was washed with 200 ml of deionized water, then resuspended in 20 ml of 5% potassium hydroxide containing 2.0 g glucose. This suspension was stirred at 80° C. for three hours, after which solid was removed by filtration, washed with 200 ml of deionized water, and dried for 16 hours at 50° C. under vacuum. The material so obtained contained 1.75% palladium.

EXAMPLE 3

A suspension of 6.4 g chitin powder in 20 ml of 0.18 M chloroplatinic acid and 20 ml of deionized water was stirred for 45 minutes. After removal by filtration, the solid was washed with 150 ml of deionized water, thereafter resuspended in 50 ml of 5% potassium hydroxide containing 2.0 g glucose, and the suspension was heated at 90° C. for three hours with stirring. Removing the solid by filtration, washing with 200 ml of deionized water and drying for 16 hours at 50° C. under vacuum gave a platinum impregnated chitin containing 0.25% platinum.

EXAMPLE 4

A mixture of 100 ml of 1-heptane and 2.0 g of catalyst as prepared in Example 3 was placed in a 250 cc stainless steel autoclave. The reactor was pressurized with hydrogen to 700 psig and maintained at 175° C. for 1.5 hours. Analysis of the product by gas liquid partition chromotography showed 36.5% 1-heptene, 49.6% n-heptane, 1.1% of trans-and cis-3-heptene, 5.0% trans-2-heptene, 2.8% cis-2-heptene, and 5% of unidentified material.

Thus the catalyst showed appreciable activity in hydrogenation, and also demonstrated an ability to isomerize terminal olefins.

What is claimed is:

1. A catalytic composition of matter comprising a support selected from the group consisting of chitin and chitosan having immobilized thereon in a highly dispersed state at least one metal in a concentration of from about 0.01 to about 10% by weight, wherein at least 51% of said metal is present in its zero-valent state.

2. The composition of claim 1 wherein each of said metals is selected from Group VIII of the periodic table.

* * * * *